US00PP14064P39

(12) United States Plant Patent
Meilland

(10) Patent No.: US PP14,064 P3
(45) Date of Patent: Aug. 19, 2003

(54) HYBRID TEA ROSE PLANT NAMED 'MEITIZADO'

(75) Inventor: Alain A. Meilland, Antibes (FR)

(73) Assignee: CP (Delaware), Inc., Wilmington, DE (US)

( * ) Notice: Subject to any disclaimer, the term of this patent is extended or adjusted under 35 U.S.C. 154(b) by 137 days.

(21) Appl. No.: 09/978,083

(22) Filed: Oct. 17, 2001

(65) Prior Publication Data

US 2002/0073451 P1 Jun. 13, 2002

(30) Foreign Application Priority Data

Oct. 19, 2000 (FR) ..... 17450

(51) Int. Cl.[7] ..... A01H 5/00
(52) U.S. Cl. ..... Plt./132
(58) Field of Search ..... Plt./130, 132, 131

*Primary Examiner*—Howard J. Locker
(74) *Attorney, Agent, or Firm*—Burns, Doane, Swecker & Mathis, LLP

(57) ABSTRACT

A new and distinct variety of Hybrid Tea rose plant is provided which abundantly forms attractive very double bicolored blossoms that are variegated orange on the upper surface and yellow on the under surface. The plant exhibits an erect growth habit, very rigid stems, dense semi-glossy decorative dark green foliage, and good resistance to Powdery Mildew and Botrytis. The attractive dark green foliage contrasts nicely with the blossom coloration. The new variety is particularly well suited for cut flower production under standard greenhouse growing conditions.

1 Drawing Sheet

SUMMARY OF THE INVENTION

Figures 1, 2, 3, 4, 5, 6, 7, 8, 9, 10, 11, 12, 13, 14, 15, 16:
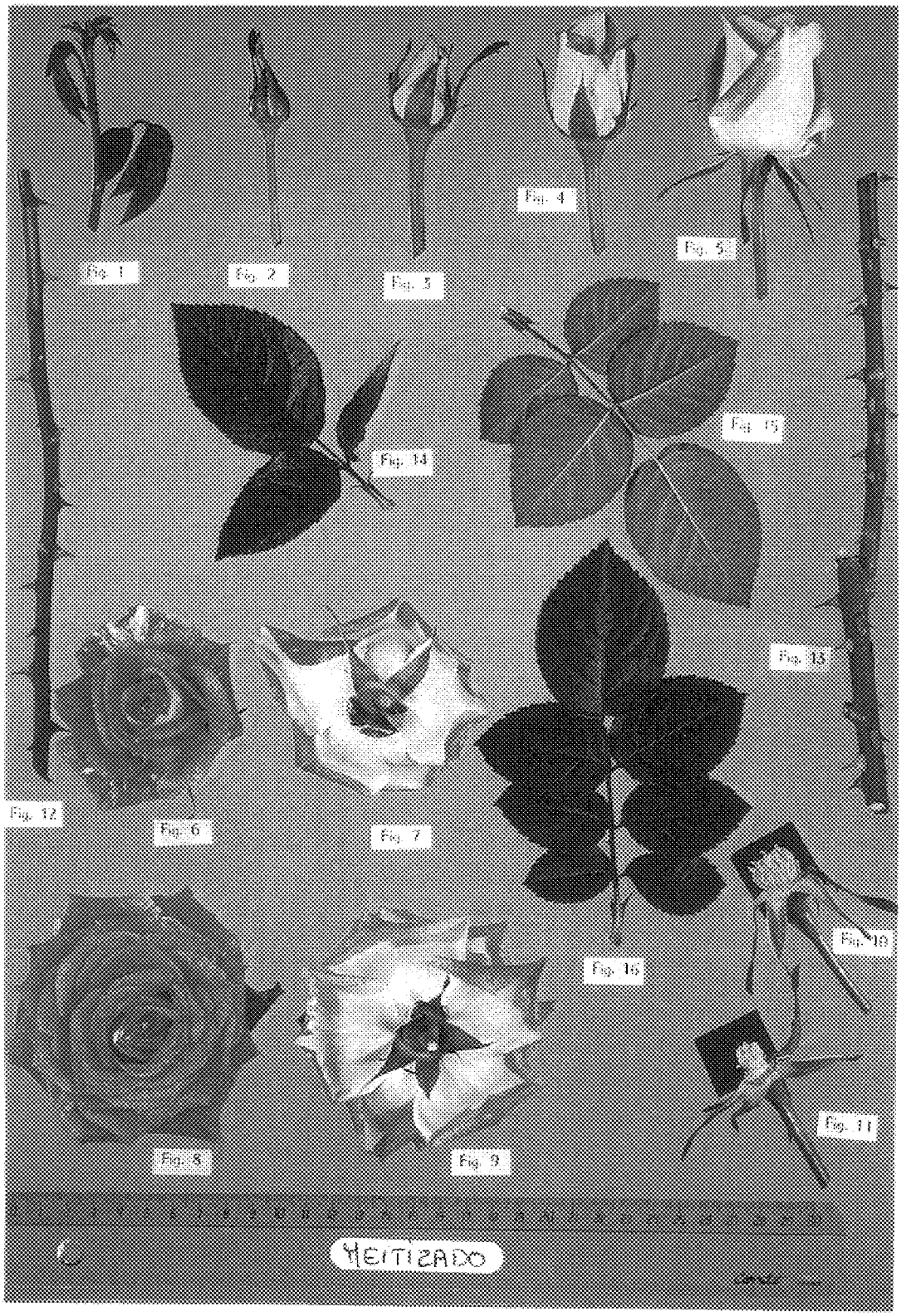

The new variety of *Rosa hybrida* Hybrid Tea rose plant was created by artificial pollination wherein two parents were crossed which previously had been studied in the hope that they would contribute the desired characteristics. The female parent (i.e., the seed parent) was the 'Korenlo' variety (U.S. Plant Pat. No. 5,679). The male parent (i.e., the pollen parent) was the 'Keitaibu' variety (U.S. Plant Pat. No. 7,739). The parentage of the new variety can be summarized as follows:

'Korenlo'×'Keitaibu'.

The seeds resulting from the above pollination were sown and small plants were obtained which were physically and biologically different from each other. Selective study resulted in the identification of a single plant of the new variety.

It was found that the new variety of the present invention (a) exhibits an erect growth habit, (b) forms very rigid stems, (c) abundantly forms very double bicolored blossoms are variegated orange on the upper surface and yellow on the under surface, (d) forms dense dark green semi-glossy foliage that contrasts well with the blossom coloration, and (e) is particularly well suited for growing for cut flower production in the greenhouse.

The disease resistance is good with respect to Powdery Mildew and Botrytis.

The new variety well meets the needs of the horticultural industry and can be used to advantage for forming distinctive cut flowers indoors. Such flowers display a powdered aspect.

The new variety has been found to undergo asexual propagation in France by a number of routes, including budding, grafting, and cuttage. Asexual propagation by the above-mentioned techniques in France has shown that the characteristics of the new variety are stable and are strictly transmissible by such asexual propagation from one generation to another.

The new variety has been named the 'Meitizado' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during April while budded on *Rosa indica* understock and growing in greenhouses at Le Cannet des Maures, Var, France. Dimensions in centimeters are indicated at the bottom of the photograph.

FIG. 1—illustrates a specimen of a young shoot;

FIG. 2—illustrates a specimen of a floral bud before the opening of the sepals;

FIG. 3—illustrates a specimen of a floral bud at the opening of the sepals;

FIG. 4—illustrates a specimen of a floral bud at the opening of the petals;

FIG. 5—illustrates a specimen of a flower in the course of opening;

FIG. 6—illustrates a specimen of an open flower—plan view—obverse;

FIG. 7—illustrates a specimen of an open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates a specimen of a leaf with three leaflets—plan view—upper surface;

FIG. 15—illustrates a specimen of a leaf with five leaflets—plan view—under surface; and FIG. 16—illustrates a specimen of a leaf with seven leaflets—plan view—upper surface.

DETAILED DESCRIPTION

The chart used in the identification of the colors is that of The Royal Horticultural Society (R.H.S. Colour Chart). The description is based on the observation of two year-old plants during September while budded on *Rosa indica* understock and growing in greenhouses at Le Cannet des Maures, Var, France.

Class: Hybrid Tea.

Plant:

*Height.*—When pruned to a height of 85 cm, floral stems having a length of approximately 70 to 80 cm commonly are produced at the end of the growing season.

*Habit.*—Erect.

Branches:

*Color.*—Young stems: near Yellow-Green Group 147A. Adult wood: near Yellow-Green Group 146B.

*Thorns.*—Size: medium (as illustrated). Quantity: moderately numerous (as illustrated). Color: near Yellow-Green Group 153A on young stems and near Greyed-Orange Group 163A to 164A on adult wood. Configuration: somewhat straight upper surface and concave under surface.

Leaves:

*Stipules.*—Adnate, pectinate, and narrow.

*Petioles.*—Upper surface: near Yellow-Green Group 147A and rather glandular with a few prickles. Under surface: near Yellow-Green Group 147D and relatively smooth.

*Leaflets.*—Number: 3, 5 (most often), and 7. Shape: somewhat ovate with a rounded base (as illustrated). Serration: simple and regular (as illustrated). General appearance: very dense, dark green, and semi-glossy. Color (young foliage): Upper surface: near Green Group 139A. Under surface: near Green Group 137C. Color (adult foliage): Upper surface: near Green Group 137A. Under surface: near Green Group 137C.

Inflorescence:

*Number of flowers.*—Usually one per stem.

*Peduncle.*—Rigid with a few prickles, near Yellow-Green Group 146C, and the length is approximately 8 cm on average.

*Sepals.*—Upper surface: tomentose and near Yellow-Green Group 139A to 139C in coloration. Under surface: glabrous and near Yellow-Green 146A in coloration. Configuration: elongated with a few extensions (as illustrated).

*Buds.*—Shape: conical. Size: medium (as illustrated). Length: approximately 5 cm on average.

*Flower.*—Shape: high-pointed. Diameter: approximately 10 cm on average. Color (when opening begins): Upper surface: near Orange Group 27B maculated with Greyed-Red Group 179A. Under surface: near Orange Group 27B. Color (when blooming): Upper surface: Orange Group 27D and irregularly maculated and suffused with Greyed-Red Group 179A and 179B, and Yellow-Orange Group 18A at the base. The external petals are striped with Orange Group 27D. Under surface: near Orange Group 27D, and near Yellow-Orange Group 18A at the base. Color (at end of opening): Upper surface: near Orange Group 27D and irregularly maculated and suffused with Greyed-Red Group 179A and 179B, and new Yellow-Orange Group 18A at the base. Under surface: near Orange Group 27D, and near Yellow-Orange Group 18A at the base. Fragrance: none. Lasting quality: very long, the blossoms commonly last approximately 15 days on average when cut and placed in a vase, and approximately 20 days on average on the plant. Petal number: approximately 50 to 55 average. Petal shape: rounded at the tip and obovate at the base with reflexed edges when fully open. Petal drop: good with the petals commonly detaching cleanly. Stamen number: approximately 70 on average. Anthers: near Yellow-Orange Group 16A in coloration. Filaments: near Yellow-Orange Group 15C in coloration. Pistils: approximately 95 on average. Stigmas: near Yellow-Orange Group 20B. Styles: near Red Group 39A in coloration. Receptacle: smooth, near Yellow-Green Group 146B in coloration, and funnel-shaped in longitudinal section.

Development:

*Vegetation.*—Vigorous and strong.

*Blooming.*—Abundant.

*Resistance to diseases.*—Good with respect to Powdery Mildew and Botrytis.

*Aptitude to bear fruit.*—Not evaluated since the variety is primarily grown for cut flower production.

*Productivity.*—Approximately 200 to 220 flowers per square meter per year under standard greenhouse growing conditions.

I claim:

1. A new and distinct variety of Hybrid Tea rose plant characterized by the following combination of characteristics:

(a) exhibits an erect growth habit, (b) exhibits very rigid stems, (c) abundantly forms very double bicolored blossoms that are variegated orange on the upper surface and yellow on the under surface, (d) forms dense dark green semi-glossy foliage that contrasts well with the blossom coloration, and (e) is particularly well suited for growing for cut flower production in the greenhouse;

substantially as herein shown and described.

* * * * *

YEITIZADO